(12) United States Patent
Malinowski et al.

(10) Patent No.: US 7,742,817 B2
(45) Date of Patent: Jun. 22, 2010

(54) HERMETIC IMPLANTABLE STIMULATOR

(75) Inventors: Zdzislaw B. Malinowski, Castaic, CA (US); Michael S. Colvin, Malibu, CA (US); Leslie I. Halberg, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 958 days.

(21) Appl. No.: 11/073,290

(22) Filed: Mar. 4, 2005

(65) Prior Publication Data
US 2006/0200200 A1 Sep. 7, 2006

(51) Int. Cl.
*A61N 1/00* (2006.01)
(52) U.S. Cl. ........................................ 607/36
(58) Field of Classification Search ............ 607/36
See application file for complete search history.

(56) References Cited

U.S. PATENT DOCUMENTS

| | | | | |
|---|---|---|---|---|
| 3,866,616 A | * | 2/1975 | Purdy et al. ................ | 607/36 |
| 4,979,019 A | * | 12/1990 | Paquette et al. ............ | 257/747 |
| 5,298,683 A | * | 3/1994 | Taylor ................ | 174/152 GM |
| 5,879,375 A | * | 3/1999 | Larson et al. .................. | 607/30 |
| 6,011,993 A | * | 1/2000 | Tziviskos et al. ............. | 607/36 |
| 6,324,428 B1 | * | 11/2001 | Weinberg et al. ............. | 607/36 |
| 7,016,721 B2 | * | 3/2006 | Lee et al. ..................... | 600/523 |
| 2006/0243483 A1 | * | 11/2006 | Kirby et al. .................. | 174/267 |

* cited by examiner

*Primary Examiner*—Scott M Getzow
(74) *Attorney, Agent, or Firm*—Vista IP Law Group LLP

(57) ABSTRACT

An implantable medical device, e.g., an implantable pulse generator, having a non-metal sealed housing and method of making same. An exemplary embodiment of the device includes a replenishable power source, coupling electronic components configured to generate a pulse signal to the replenishable power source, and an inorganic coating covering the electronic components and the power source to seal, preferably hermetically, the electronic components and the power source from a body environment.

26 Claims, 8 Drawing Sheets

HERMETIC IMPLANTABLE STIMULATOR

BACKGROUND

Spinal cord stimulation systems and other stimulation devices frequently utilize an implantable pulse generator (IPG) for treating chronic pain by delivering electrical stimulation pulses from an electrode array placed epidurally near a patient's spine. Spinal cord stimulation (SCS) is a well-accepted clinical method for reducing pain in certain populations of patients. SCS systems typically include an IPG and at least one stimulating lead having one or more electrode contacts (an electrode array) connected to the lead.

Electrical pulses may be delivered to the dorsal column fibers within the spinal cord through the electrode contacts which are implanted along the dura of the spinal cord. In a typical situation, the attached stimulation lead exit the spinal cord and are tunneled around the torso of the patient to a sub-cutaneous pocket where the pulse generator may be implanted.

In order to protect the electronic circuitry from environmental conditions and/or other damage while the IPG is implanted within a patient, the IPG is frequently enclosed in a hermetic, titanium case to provide protection from the body environment. Traditionally, the titanium case includes two halves. Recesses are formed in each of the halves such that when the two halves are coupled together, holes are formed. Feedthrus extend through these holes to the outside, which feedthrus are electrically coupled to the electronic circuitry located within the IPG.

In particular, to properly establish the feedthrus, the titanium halves often must be aligned with respect to each other and with respect to the feedthru. Once aligned, the assembly is welded and checked for leaks. If the resulting assembly is not hermetically sealed, the assembly is reworked. Even if the assembly is sealed during formation, it may be possible for the titanium case to leak where it interfaces with the feedthrus. If the titanium case does leak, resulting in the ingress of moisture, the IPG may fail prematurely due to damage of the electronic circuit within the IPG.

Further, some designs allow the battery that powers the IPG to be recharged through an inductive coupling using an external power source. The use of a titanium case may partly shield the power transmission and limit the rate at which the battery may be charged. More specifically, eddy currents may be generated within the titanium case during inductive power transmission. The production of eddy currents reduces the efficiency of power transmission and can cause the titanium case to heat up to an undesirably hot temperature.

SUMMARY

An implantable stimulator device (or an IPG) and method of making the devices are provided. The stimulator device may include a replenishable power source, and a circuit board populated by various electronic components for generating an electrical stimulus. The stimulator device may be made by applying an inorganic coating to the electronic components and to a power source to provide a seal, which seal is preferably hermetic.

BRIEF DESCRIPTION OF THE DRAWINGS

The accompanying drawings illustrate various embodiments of the present apparatus and method and are a part of the specification. The illustrated embodiments are merely examples of the present apparatus and method and do not limit the scope of the disclosure.

Throughout the drawings, identical reference numbers designate similar, but not necessarily identical, elements.

DETAILED DESCRIPTION

Methods, apparatuses, and systems for use in spinal cord stimulation are described herein. These methods, apparatuses, and systems make use of an implantable pulse generator (IPG) that may be hermetically enclosed in a non-metallic composite. As will be discussed in more detail below, such use of a non-metallic composite to seal the internal components of an IPG may accomplish one or more of the following: (1) simplify the process of assembling an IPG, (2) reduce the number of processing steps for manufacturing an IPG, (3) allow a faster charging rate due to a reduction in heating, (4) result in a smaller overall IPG size, and/or (5) increase its reliability. An exemplary neuro-stimulation system will be discussed that includes an IPG that is sealed, preferably hermetically, with a non-metallic composite. Thereafter, an exemplary IPG will be discussed in more detail followed by a discussion of an exemplary method of forming the IPG.

In the following description, for purposes of explanation, numerous specific details are set forth in order to provide a thorough understanding of the present method and apparatus. It will be apparent, however, to one skilled in the art, that the present method and apparatus may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Spinal Cord Stimulation System

Figure 1:
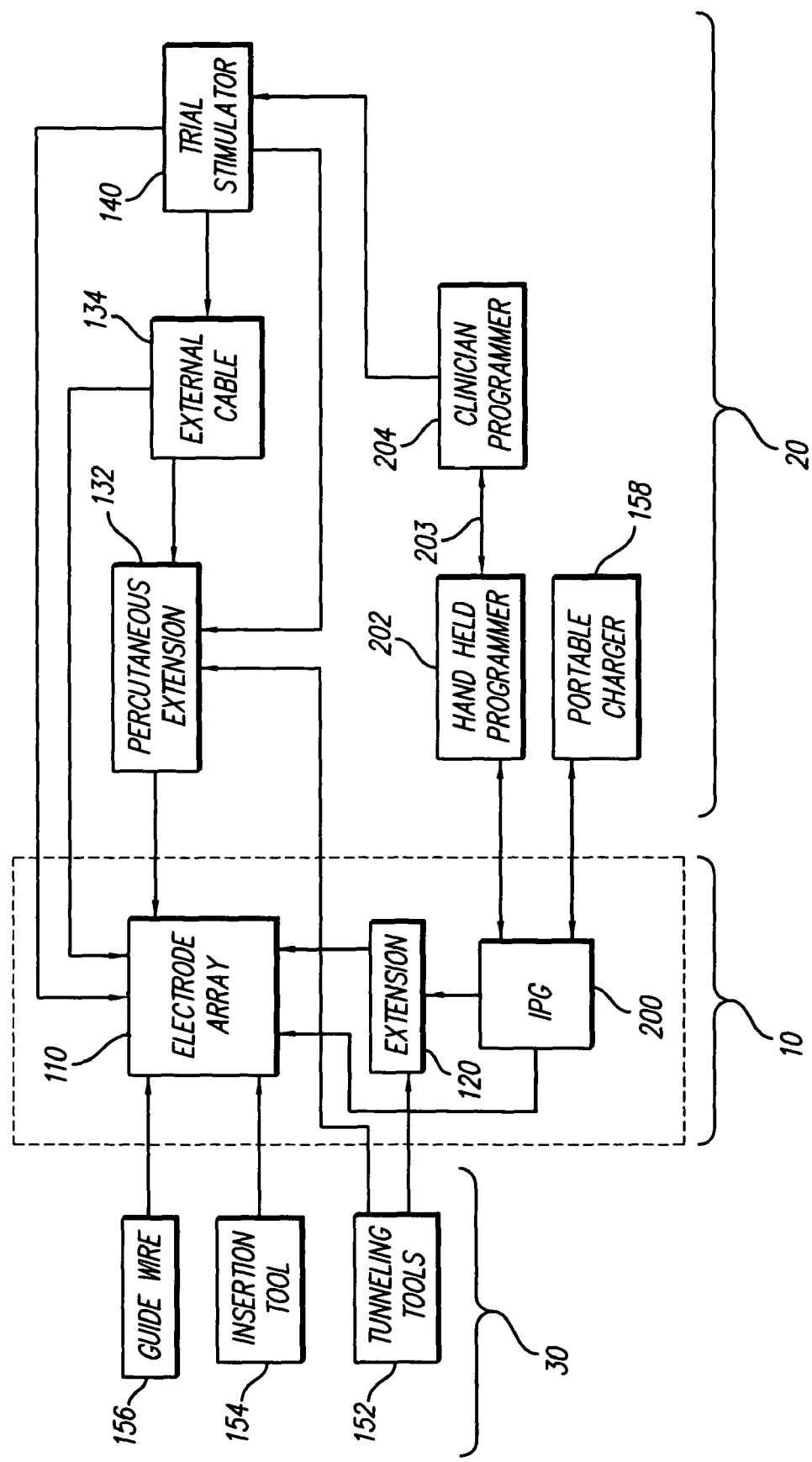
FIG. 1 is a schematic view of an implantable stimulator system having external and implantable components, according to one exemplary embodiment.

FIG. 1 is a block diagram illustrating several exemplary components that may be used in an exemplary stimulation system, such as a spinal cord stimulation (SCS) system. While the stimulation system will be described with reference to a spinal cord stimulation system, those of skill in the art will appreciate that the stimulator system can be applied to other areas of the human body. The components of the exemplary stimulation system may be subdivided into three broad categories: implantable components (10), external components (20), and surgical components (30).

As seen in FIG. 1, the implantable components (10) may include an implantable pulse generator (IPG) (200), an electrode array (110) which is an array of electrode contacts, and an optional lead extension (120). As will be discussed in more detail below, the implantable stimulator device or an implantable pulse generator or "IPG" (200) may be hermetically sealed within a non-metallic composite coating. The use of such a coating, instead of a metal cover, may simplify the method of manufacturing the IPG (200), as well as potentially increase the rate of inductive charging of an enclosed rechargeable battery by avoiding eddy currents generated in metal housings, such as ones made from titanium. Further, the use of such a coating may allow for a smaller overall size of the IPG while increasing the reliability of such a device.

The implantable lead extension (120) may optionally be used to electrically couple the electrode array (110), which is part of stimulating lead, to the IPG (200). In an exemplary embodiment, the IPG, described more fully below, may be a multi-channel, e.g., eight or sixteen channel, telemetry-controlled, stimulator. A tool-less lead connector may also be part of the IPG.

The electrode array (110) and its associated lead system can electrically connect with the IPG (200) via a lead extension system (120). As needed, for testing and/or fitting purposes, the electrode array (110) may also interface with an external trial stimulator (ETS) (140) through one or more percutaneous lead extensions (132), connected to the trial stimulator (140) through an external cable (134). In this manner, the individual electrode contacts included within the electrode array (110) may receive an electrical stimulus from either the trial stimulator (140) or the IPG (200), but not at the same time.

As suggested in the block diagram of FIG. 1, the lead extension(s) (120), as well as the percutaneous extension(s) (132) are inserted through the patient's tissue through the use of appropriate surgical tools (ST) (30). In particular, the lead extension(s) (120) and the percutaneous extension(s) (132) may be inserted through the use of tunneling tools (152). In a similar manner, the electrode array (110) may be implanted in its desired position adjacent to the spinal column of the patient through the use of an insertion needle (154) and a guide wire (156). The insertion needle, according to one exemplary embodiment, may be a 15-gauge Touhy needle.

Additionally, a lead blank may be used to aid in the insertion process. A lead blank is a somewhat flexible wire that approximates the lead diameter of the lead that is to eventually be implanted. A clinician uses the lead blank to clear the path through the insertion needle and into the epidural space before inserting the epidural electrode array. Use of the lead blank prevents damage to the electrode array when tissue is obstructing its insertion path.

Typically, the IPG (200) is placed in a surgically-made pocket either in the abdomen or just at the top of the buttocks. The IPG (200) may, of course, also be implanted in other locations of a patient's body. It is noted that while the exemplary IPG (200) shown includes a rechargeable battery as its power source, and while such a rechargeable power source is described herein, any power source may be used with the IPG (200), including non-rechargeable, primary, power sources, such as an implantable battery of the type commonly used in implantable pacemakers.

Once a stimulating lead having the electrode array (110) is properly implanted, the IPG may be connected to the stimulating lead. One exemplary lead system includes the lead extension (120), if needed, and the electrode array (110) on a stimulating lead. Once implanted, the electrode array (110) and lead extension (120) are intended to be permanent. In contrast, the IPG (200) may be replaced when its power source fails or is no longer rechargeable.

A handheld programmer (202) and/or portable charger (158) may also be telecommunicatively coupled to the IPG (200) to provide programming and recharge the power source of the portable charger. A clinician programmer (204) may also be used to access the hand-held programmer to control the operation of the IPG (200).

Implantable Pulse Generator

Figure 2:
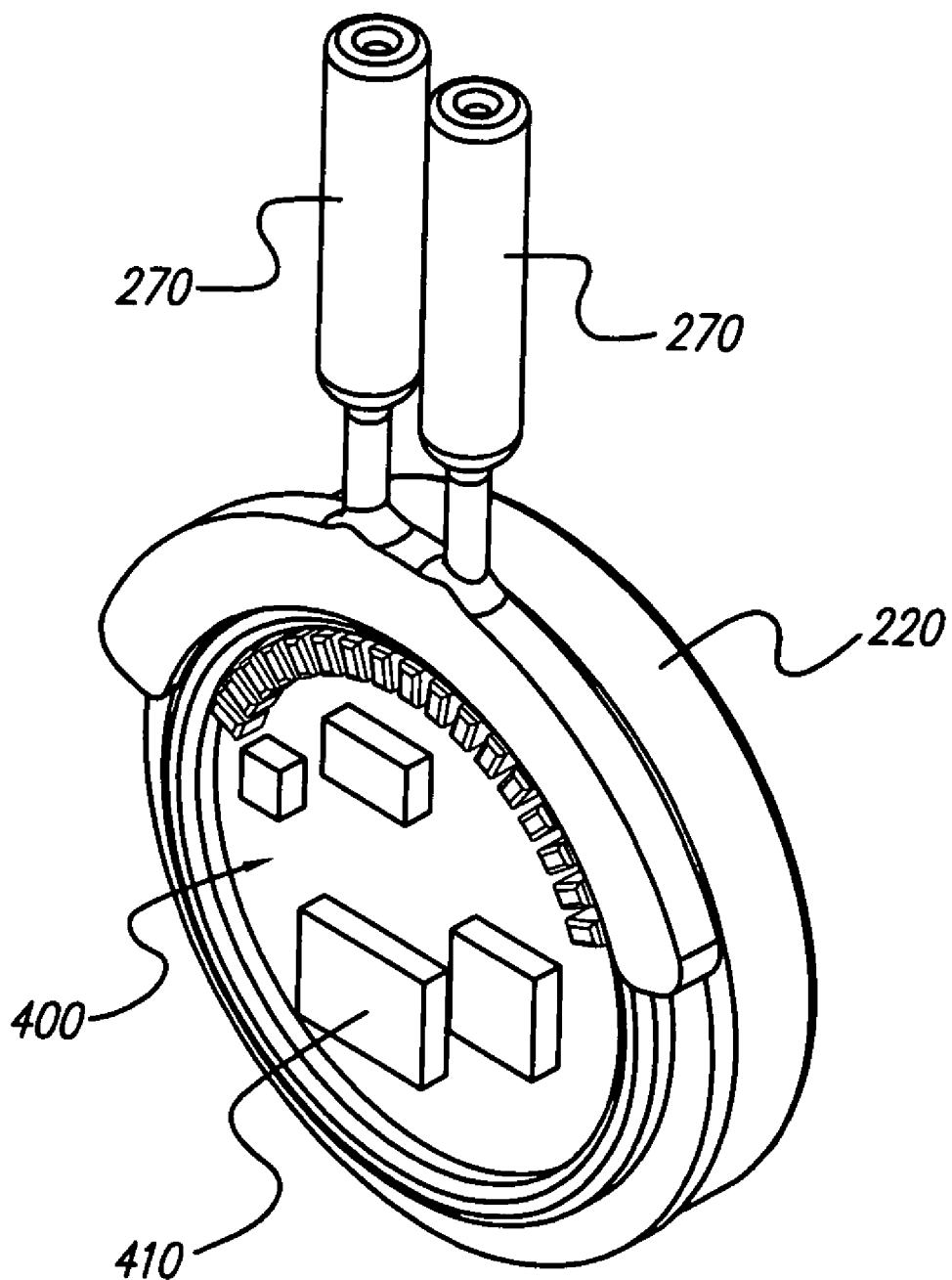
FIG. 2 is a perspective view showing a partial assembly of an IPG showing lead connectors, battery and circuit board.

FIG. 2 is a perspective view of an IPG assembly showing a circuit board or hybrid (400) and lead connectors (270) attached to the connector assembly. The circuit board may be electrically connected to a power source (220), e.g., a replenishable power source, such as a rechargeable battery or a primary, non-rechargeable battery. The exemplary components (410) populated on the circuit board (400) may include a microprocessor, a power circuit, and/or a clock circuit.

According to the present exemplary embodiment, the circuit board (400) and the power source (220) may be sealed within a non-metallic composite, which seal may be hermetic. The sealed, non-metallic composite coating may then be further coated with several coatings, such as a layer of impact resistant epoxy and/or a soft material or resilient material.

The above-mentioned configuration provides for a robust and sealed IPG (200) that is of relatively small size. Further, the IPG design may be formed using efficient methods of manufacture. Additionally, such a configuration may allow for a faster charging rate of a rechargeable battery (220) because the non-metallic composite coating does not host energy robbing eddy currents.

Method of Forming an Implantable Stimulator Device

Figure 3:
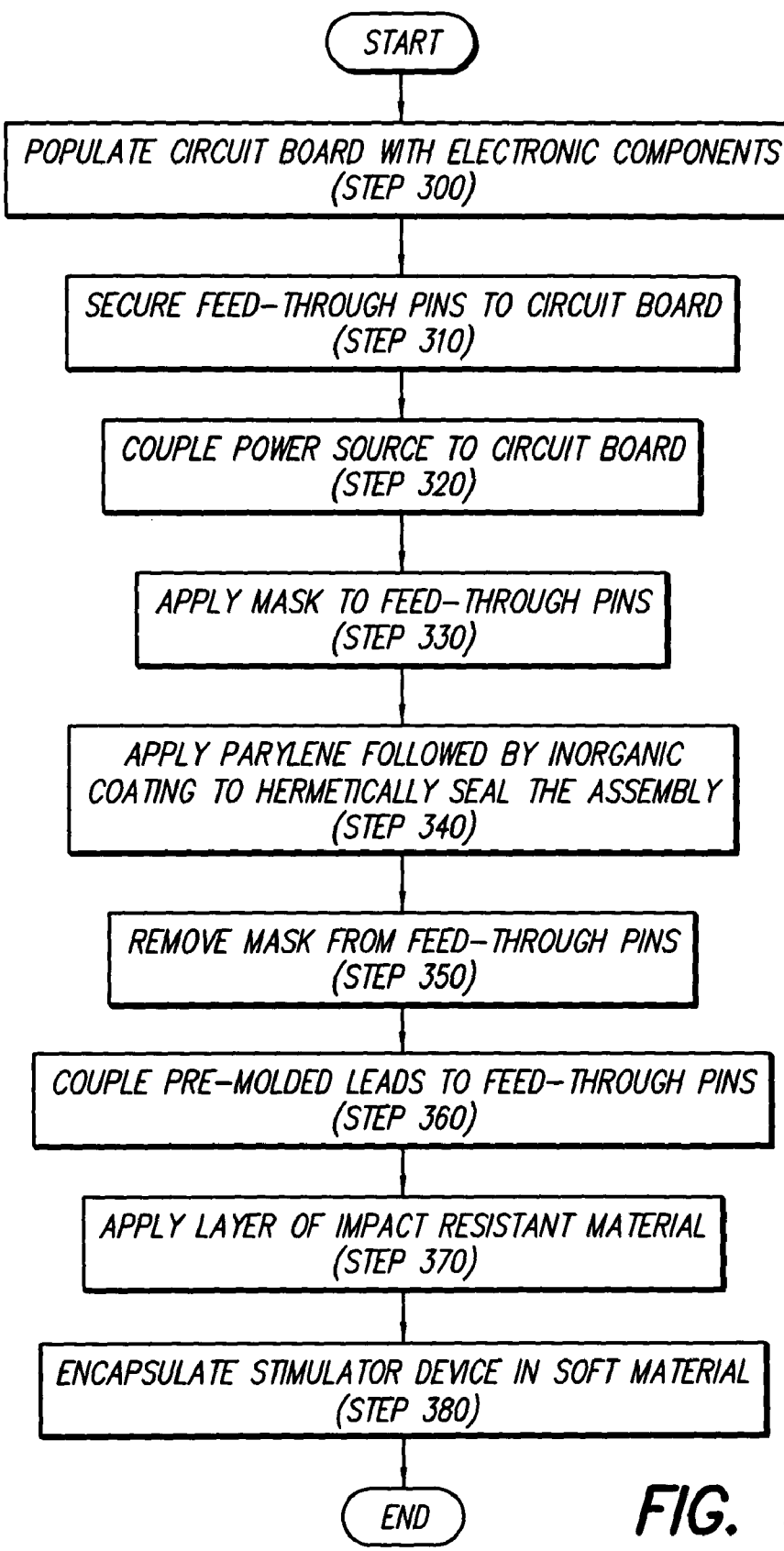
FIG. 3 is a flowchart of a method of forming an implantable stimulator device or an IPG, according to one exemplary embodiment.

FIG. 3 is a flowchart illustrating a method for forming an implantable stimulator device, according to one exemplary embodiment. The exemplary method illustrated in FIG. 3 begins by populating an electronic circuit board with a number of desired electronic components (step 300). Once the desired electronic components are secured to the electronic circuit board (step 300), a number of feedthru pins are secured to the electronic circuit board (step 310). A power source is then electrically coupled to the electronic circuit board (step 320) followed by the application of a mask to the feedthru pins (step 330). With the mask securely applied to the feedthru pins (step 330), parylene and an inorganic coating are applied to the assembly to hermetically seal the assembly (step 340). With the assembly hermetically sealed, the mask is removed (step 350) and a connector assembly having a pair of pre-molded lead connectors is coupled to the feedthru pins (step 360) on the circuit board. After the connector assembly is coupled to the feedthru pins (step 360), a layer of impact resistant material may be disposed on this intermediate assembly (step 370) followed optionally by a further encapsulation of the intermediate assembly with a soft material (step 380). The above described method will be described in further detail below with reference to FIGS. 4A through 6.

Figure 4A:
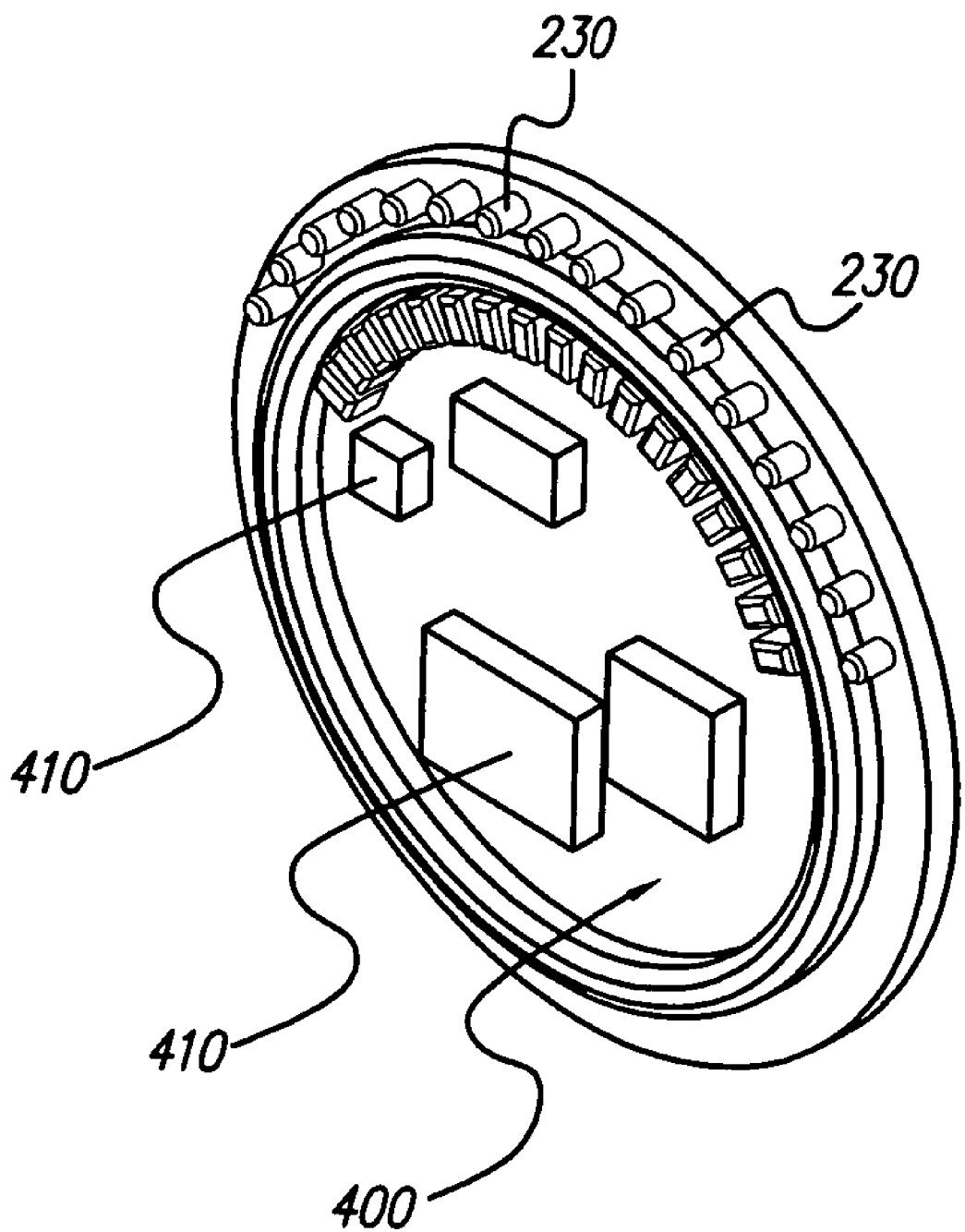
FIG. 4A is a perspective view illustrating a circuit board or hybrid and feedthru pins that may be included, according to one exemplary embodiment.
Figure 5:
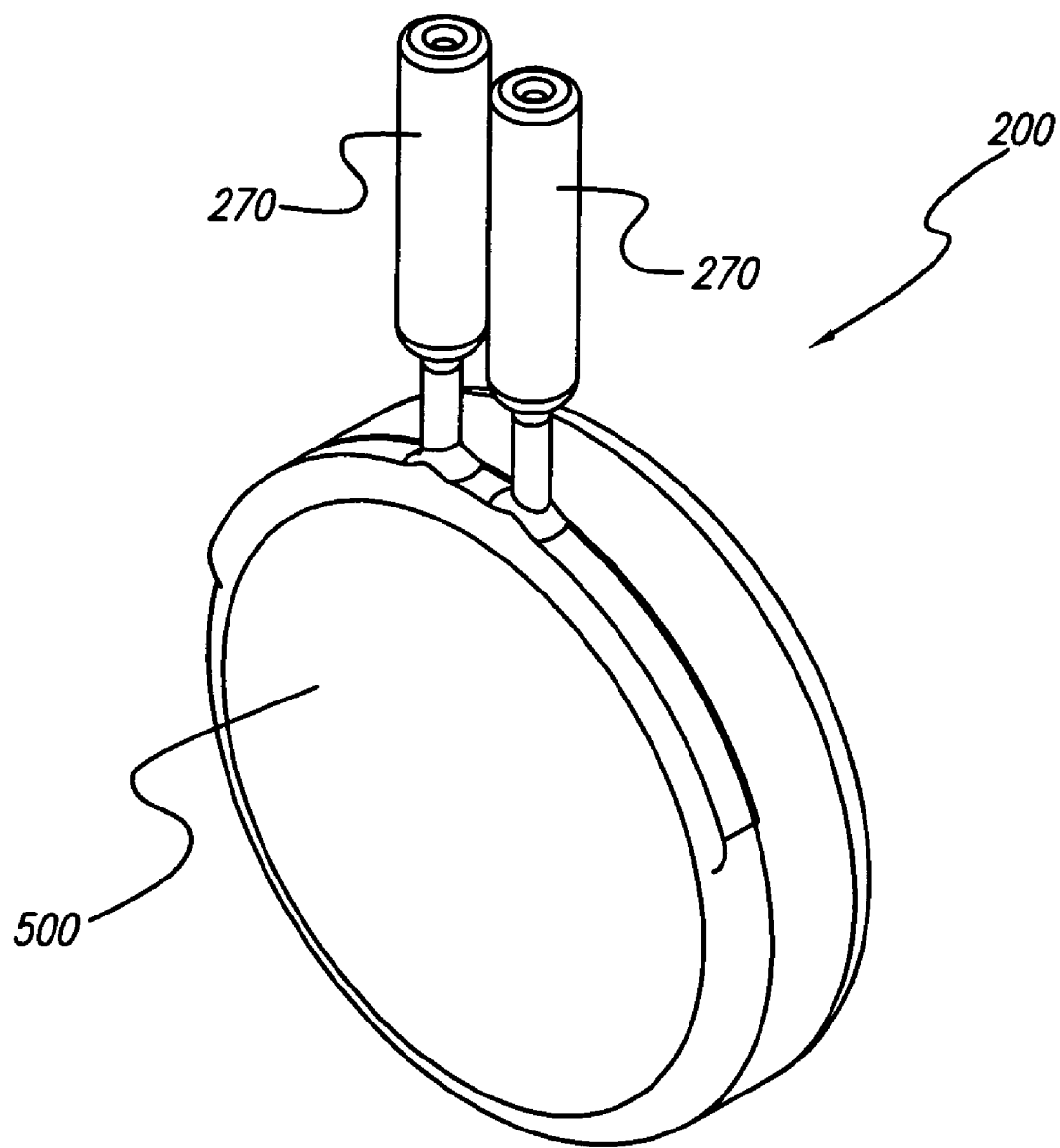
FIG. 5 is a front, perspective view of an IPG covered in an impact resistant material, according to one exemplary embodiment.
Figure 6:
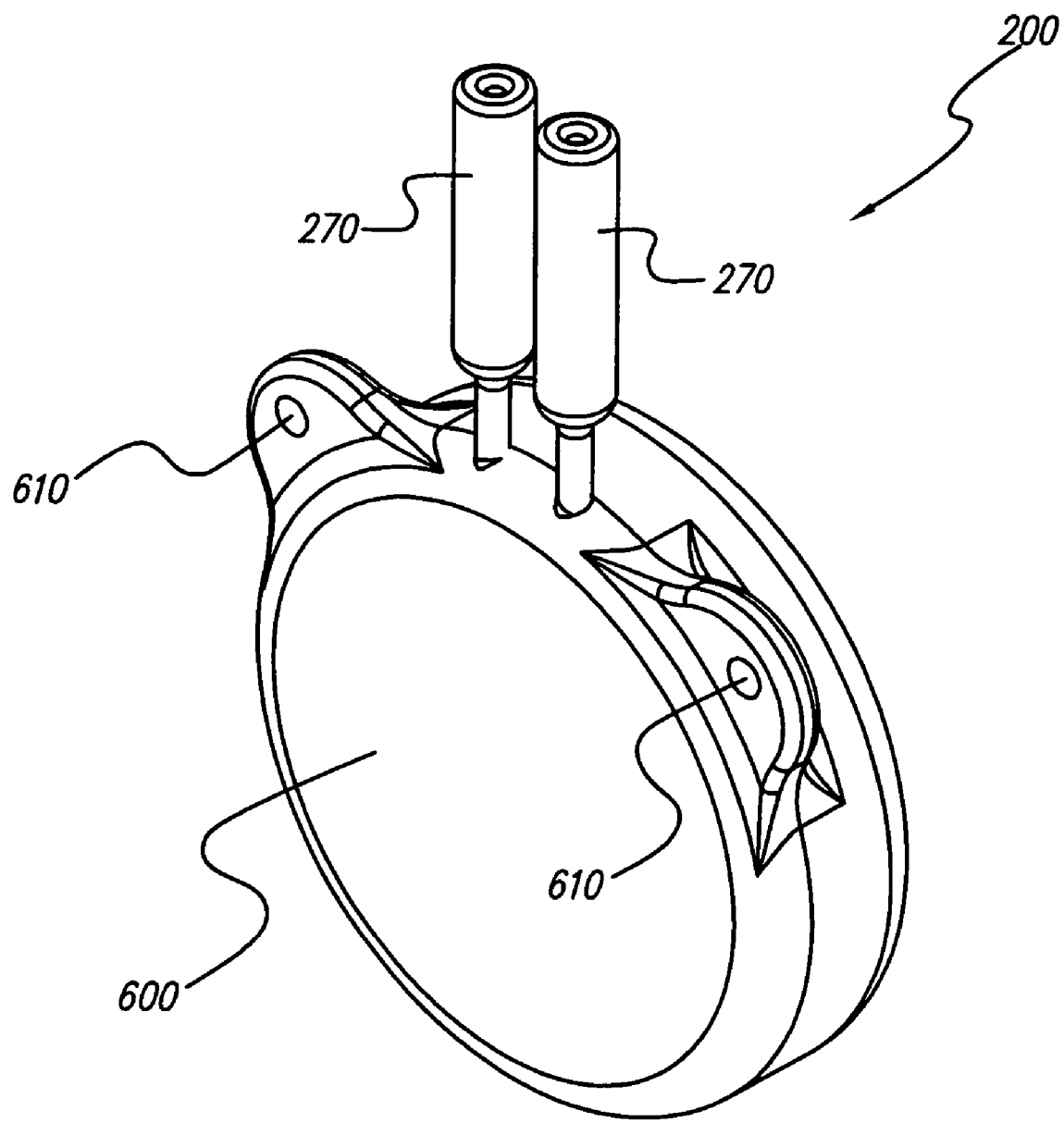
FIG. 6 is a front perspective view of an IPG further encapsulated in a soft material, the soft material having suture holes, according to one exemplary embodiment.

As illustrated in the flowchart of FIG. 3, the present exemplary method begins by first populating an electronic circuit board with a number of desired electronic components (step 300). FIG. 4A illustrates an exemplary circuit board or hybrid (400), according to one embodiment. As illustrated in FIG. 4A, the circuit board or hybrid (400) is populated with a number of electronic components (410). According to one exemplary embodiment, the electronic components (410) are secured to the electronic circuit board or hybrid (400) either manually or by automated processes. The electronic components (410) may include, but are in no way limited to, a microcontroller coupled to a memory circuit. An exemplary microcontroller that may be associated with the present IPG (200; FIGS. 1, 5, 6) includes a microprocessor and associated logic circuitry, which in combination with control logic circuits, timer logic, and an oscillator and clock circuit, generates control and status signals that allow the microcontroller to control the operation of the IPG, in accordance with a selected operating program and stimulation parameters.

Another electronic component that may populate the electronic circuit board or hybrid (400) is a memory circuit. The operating program and stimulation parameters of the IPG are typically programmably stored within the memory circuit by transmitting an appropriate modulated carrier signal through a receiving coil and charging a forward telemetry circuitry from an external programming unit, such as a handheld programmer (HHP) and/or a clinician programmer (CP), assisted as required through the use of a directional device. The handheld programmer may thus be considered to be in "telecommunicative" contact with the IPG. Similarly, the clinician programmer is considered to be in telecommunicative contact with the handheld programmer and, through the handheld programmer, with the IPG. The charging and forward telemetry circuitry demodulates the carrier signal it receives through the coil to recover the programming data (for example, the operating program and/or the stimulation parameters), which programming data is then stored within the memory circuit or within other memory elements distributed throughout the circuit board or hybrid (400).

Additionally, a microcontroller may be coupled to the circuit board or hybrid (400) where it may be electrically coupled to monitoring circuits via a bus. According to this exemplary embodiment, the monitoring circuits monitor the status of various nodes or other points throughout the IPG (e.g., power supply voltages, current values, temperature, the impedance of electrodes attached to the various electrodes, and the like). Informational data sensed through the monitoring circuit may be sent to a remote location external to the IPG (e.g., a non-implanted location) through back telemetry circuitry, including a transmission coil.

Further, the exemplary circuit board or hybrid (400) may also include power circuits. According to one exemplary embodiment, the power circuits may include protection circuitry that protects a replenishable power source, e.g., a rechargeable battery, from overcharging. Further, safeguarding features may be incorporated in the exemplary circuit board or hybrid that help assure that the power source is operated in a safe mode upon approaching a charge depletion. Potentially endangering failure modes are reduced and/or prevented through appropriate logic control that is hard-wired into the device or otherwise set in the device in such a way that a patient cannot override them.

Once the electronic components (410) are secured to the electronic circuit board or hybrid (400) a number of feedthru pins (230), are secured to the electronic circuit board or hybrid (step 310; FIG. 3). The feedthru pins (230) may be secured to the electronic circuit board or hybrid (400) such that they are in electrical contact with a number of electrical traces leading to the electronic components (410). The feedthru pins (230) and the electronic components may be secured to the electronic circuit board or hybrid (400) by a cure hardening compound, such as a hard polymer, epoxy, or other such material. Once secured to the electronic circuit board or hybrid (400), the electronic components (410) and the feedthru pins (230) may be electrically tested and the circuit board or hybrid (400) may be dried. The assembly may be dried in a vacuum oven operating at approximately 100 to 150 degrees Celsius for up to 48 hours. Drying the exemplary assembly in a vacuum evaporates excess moisture from the electronic circuit board or hybrid (400).

Once the electronic components are secured to the circuit board and the feedthru pins (230) are secured to the circuit board or hybrid (step 310), a power source, e.g., a rechargeable battery, may be coupled to the circuit board (step 320). According to one exemplary embodiment, the rechargeable battery may be mechanically coupled to a surface of the circuit board or hybrid (400) opposite the electronic components (410). The power source (220) may be coupled to hybrid (400) by soldering or by the use of conductive epoxy.

According to one exemplary embodiment, the replenishable power source (220) may be a rechargeable battery and/or a supercapacitor. Such a power source provides an unregulated voltage to power circuits described above. The power circuits, in turn, generate the various voltages, some of which are regulated and some of which are not, as needed by the various circuits located within the IPG. The power circuits further selectively direct energy contained within the carrier signal, obtained through the charging and forward telemetry circuit, to the replenishable power source, e.g., a rechargeable battery (220), during a charging mode of operation. In this manner, the battery may be recharged.

According to one exemplary embodiment, the replenishable power source (220) is a rechargeable battery, and more particularly, is a rechargeable Lithium Ion battery. The replenishable power source (220) may be, according to one embodiment, recharged inductively from an external charging station. Further, an internal battery protection circuitry may be used for safety reasons, such as to prevent the battery from being overcharged and/or to only accept a charge from an authorized charging device.

Additionally, the IPG (200; FIGS. 1, 5, 6) may be able to monitor and telemeter the status of the replenishable power source (220) each time a communication link is established with the external patient programmer. Such monitoring not only identifies how much charge is left, but also total charge capacity. Typically, a telecommunicative link is established, and hence battery monitoring may occur each time a programming event occurs. In other words, a telecommunicative link is established each time a patient or medical personnel changes a stimulus parameter or initiates a charging operation.

As introduced previously, according to the present exemplary method, the replenishable power source (220) and circuit board with its electronic components (410) may be hermetically sealed with a non-metallic composite. Such a configuration may increase the relative speed of a recharging operation. In addition, the use of a non-metallic composite may reduce heating within the covering or case due because a non-metallic covering, in contrast to metal cases such as titanium, do not permit eddy currents. Consequently, because no energy is robbed by eddy currents, the replenishable power source, e.g., rechargeable battery (220) may be more rapidly recharged. The sealed non-metallic composite will now be discussed. For ease of reference, the combination of the replenishable power source (220) and the hybrid circuit (410) will be referred to herein as the "IPG assembly".

Once the IPG assembly has been formed, a mask is applied to the feedthru pins (step 330). The mask covers the feedthru pins (230; FIG. 4A) such that subsequent layers of material that are deposited on the assembly are deposited substantially on the mask. Suitable masks include, but are in no way limited to, silicone boots, adhesive tape, or wax.

With the mask correctly applied to the feedthru pins (230), parylene and an inorganic coating may then be applied to the IPG assembly and the masked feedthru pins, thereby hermetically sealing the IPG assembly (step 340). As mentioned, the inorganic coating is applied to the IPG assembly in such a fashion as to seal the assembly, and depending on the inorganic coating the seal may be hermetic. According to one exemplary embodiment, the inorganic coating may be deposited by reactive sputtering. Suitable inorganic coatings include, without limitation, silicon nitride, silicone dioxide, and/or silicon oxinitride. Accordingly, the inorganic coating surrounds and seals the IPG assembly, except at the feedthru pins, which are masked.

Figure 4B:
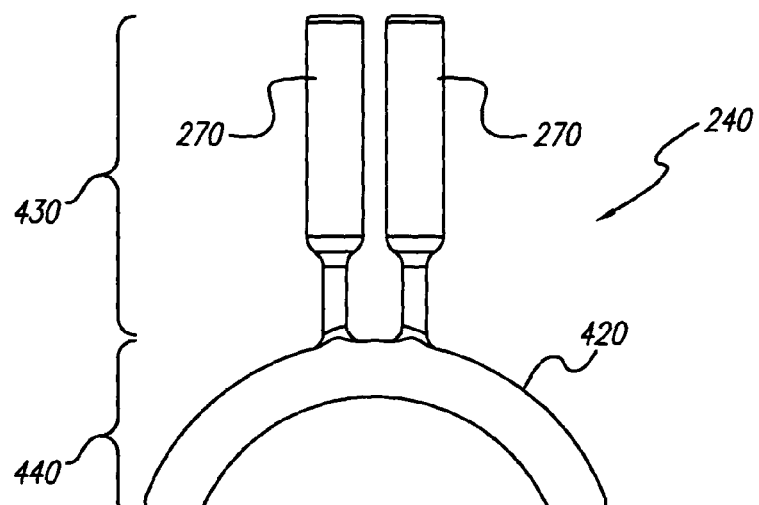
FIG. 4B is, in accordance with one embodiment, a front view illustrating an exemplary connector assembly with two lead connectors.
Figures 4C, 4D:
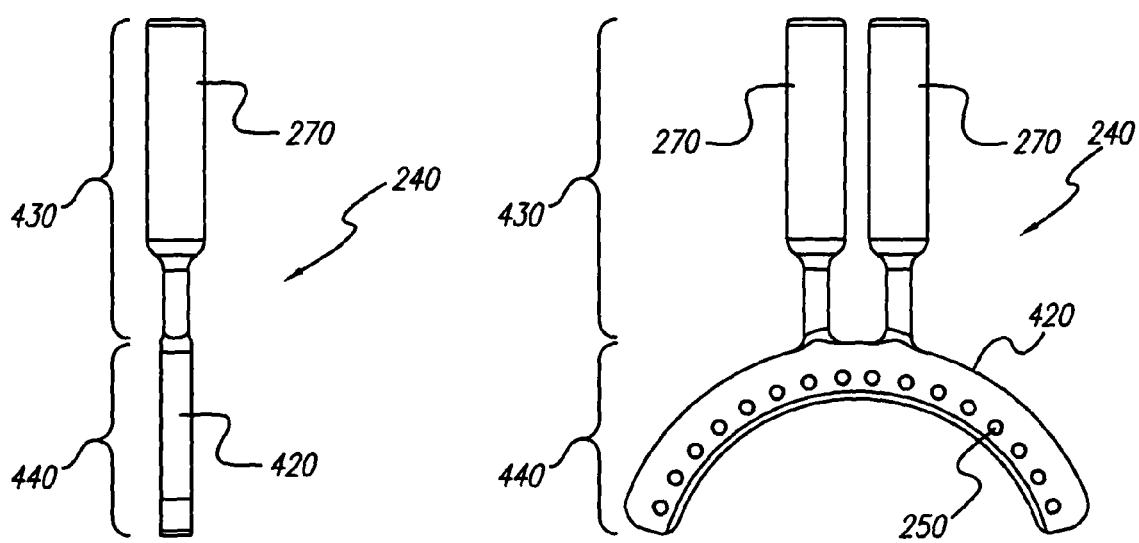
FIG. 4C is a side view of the connector assembly of FIG. 4B.
FIG. 4D is a rear view of the connector assembly of FIG. 4B, showing holes for receiving feedthru pins.

With the IPG assembly thus sealed, the mask is then removed from the feedthru pins (step 350) such that they are exposed. According to the present exemplary method, a pre-molded lead assembly with a pair of lead connector is then coupled to the feedthru pins (step 360), as illustrated in FIG. 2. As illustrated in the exemplary embodiment of FIG. 2, the pre-molded connector assembly with a pair of lead connectors (270) is disposed on the IPG assembly such that it forms an electrical connection with the feedthru pins (230; FIG. 4A). FIGS. 4B through 4F further illustrate the components of the exemplary pre-molded, connector assembly (240) according to one exemplary embodiment. As illustrated in FIGS. 4B through 4D, the pre-molded, connector assembly (240) includes, but is not limited to, a lead connector portion (430) and a portion for accepting feedthrus (440). According to the illustrated embodiment, the feedthru accepting portion (440) includes a feedthru pin coupler (420). The lead connector portion (430) includes at least one lead connector (270).

Figure 4F:
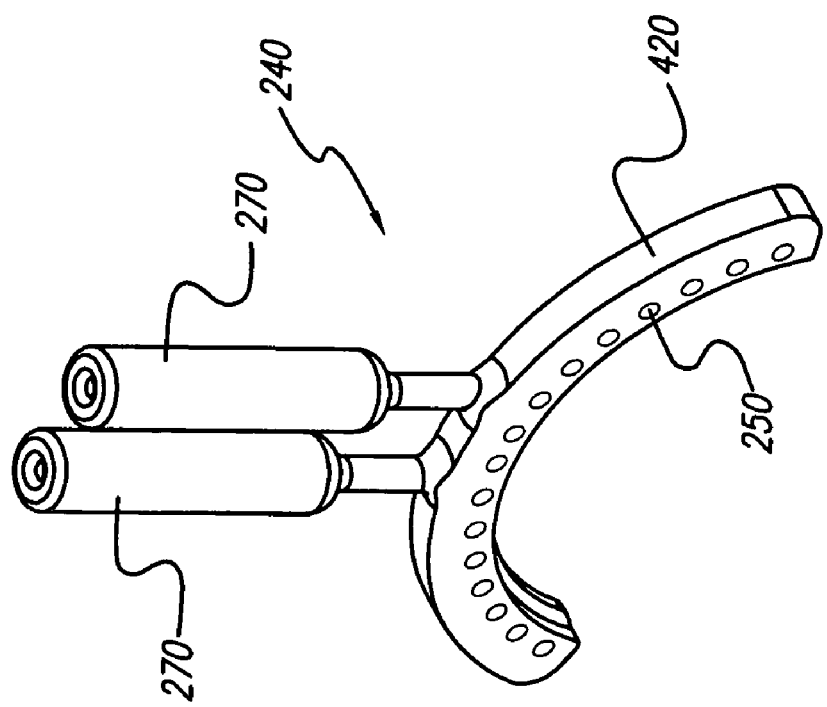
FIG. 4F is a rear, isometric view of the connector assembly of FIG. 4B.
Figure 4E:
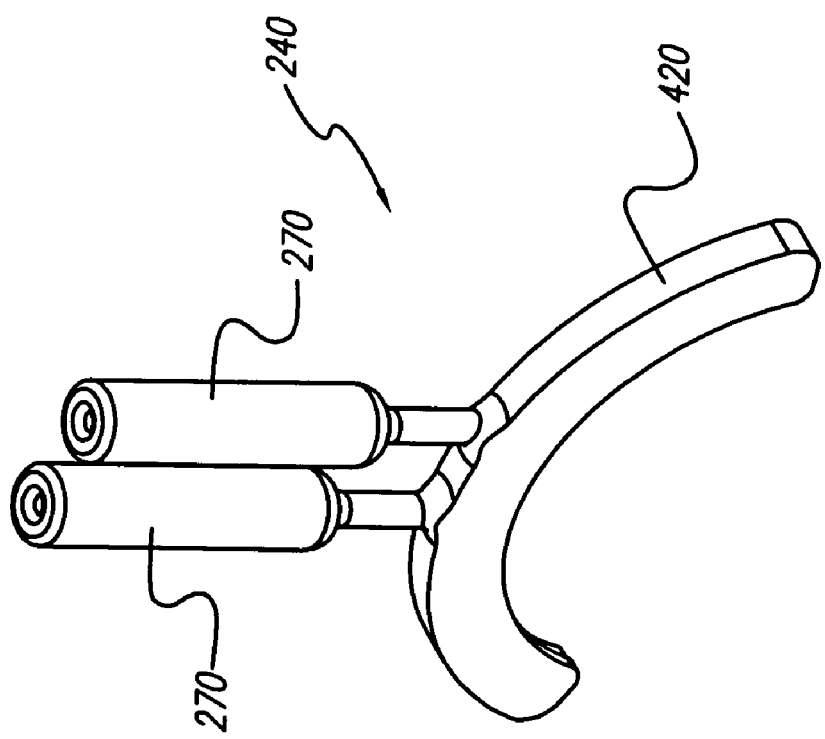
FIG. 4E is a front, isometric view of the connector assembly of FIG. 4B.

The structure of the exemplary feedthru pin coupler (420) is further illustrated by the rear view of FIGS. 4D and 4F. As illustrated, the feedthru pin coupler (420) includes a number of holes (250) having contacts within for accepting and contacting feedthru pins (230; FIG. 4A). According to one exemplary embodiment, the holes (250) with contacts within are positioned in the feedthru pin coupler (420) such that they complement the position of the feedthru pins (230) disposed on the circuit board or hybrid (400). According to one exemplary embodiment, the position of the holes (250) are such that when the feedthru pin coupler (420) is coupled to the circuit board or hybrid (400), each contact within the hole (250) is conductively coupled to a corresponding feedthru pin (230). The contacts within the holes (250) may be coupled to the feedthru pins by any suitable method including, without limitation, pressing and welding the contacts inside the feedthru holes (250) or using conductive epoxy to secure the contacts within the holes (250) to the feedthru pins (230).

Additionally, as illustrated in FIGS. 4B through 4F, the lead connector portion (430) of the exemplary pre-molded connector assembly (240) includes at least one lead connector (270) having one or more lead contacts disposed therein (not shown). According to one exemplary embodiment, the one or more lead connector (270) are configured to be coupled to a stimulation lead or a lead extension. According to one exemplary embodiment, suitable lead connectors (270) include, without limitation, plastic silastic connectors. The exemplary embodiment shown in FIGS. 4B through 4F illustrates two lead connectors (270) having conductive contacts (not shown) formed therein for contacting a stimulating lead or lead extension.

As previously discussed, the lead connector may be used to couple the IPG assembly to lead extensions and stimulating leads implanted within a patient. Thus, the sealed IPG may be part of a stimulation system, such as previously discussed with reference to FIG. 1.

According to the present exemplary method, once the pre-molded lead connectors and connector assembly are coupled to the feedthru pins, a layer of impact resistant material may be applied to the implantable stimulator device (step 370; FIG. 3). Suitable impact resistant material may include, without limitation, a relatively thick layer of impact resistant epoxy. FIG. 5 illustrates the IPG assembly disposed within a layer of impact resistant material (500), according to one exemplary embodiment. As illustrated in FIG. 5, the impact resistant material (500) may cover the entire IPG assembly as well as part of the pre-molded connector assembly (240).

Once the layer of impact resistant material has been applied to the implantable stimulator device (step 370; FIG. 3), the stimulator device may optionally be encapsulated in a soft material (step 380; FIG. 3). FIG. 6 illustrates the completed IPG and connector assembly encapsulated in a soft material (600), according to one exemplary embodiment. A suitable soft material encapsulation (600) may include, without limitation, silicone rubber. Additionally, according to one embodiment, the soft material may have suture holes (610) defined therein. The suture holes may be used to suture the IPG to tissue and secure the IPG within a desired location in a patient's body.

Methods, apparatuses, and systems for use in spinal cord stimulation are described herein. These methods, apparatuses, and systems relate to an implantable pulse generator (IPG) that is sealed in a non-metallic composite covering. As mentioned, such use of a non-metallic composite to hermetically seal the implantable stimulator device may simplify the process of assembling the implantable stimulator device, may reduce the number of processing steps for manufacturing an implantable stimulator device, may allow a faster charging rate due to elimination of heating, may result in smaller overall size of the implantable stimulator device, and may increase the reliability of the IPG.

According to one exemplary embodiment, feedthru pins used to couple the circuit board to contacts within the lead connectors are protected by a composite seal resulting in an additional barrier for safety. When this configuration is used, it can eliminate the need for welding the feedthru to the contacts in the connector assembly.

The preceding description has been presented only to illustrate and describe the present method and apparatus. It is not intended to be exhaustive or to limit the disclosure to any precise form disclosed. Many modifications and variations are possible in light of the above teaching. It is intended that the scope of the disclosure be defined by the following claims.

What is claimed is:

1. A method of forming an implantable medical device, comprising:

providing an electronic assembly comprising a circuit board and one or more electronic components mounted on the circuit board;

electrically coupling a feedthru pin to the electronic assembly;

applying a mask to a portion of the feedthru pin;

encapsulating the electronic assembly with a non-metallic hermetic composite after the mask has been applied to the feedthru pin to seal the electronic assembly from a body environment;

removing the mask from the feedthru pin to expose the portion of the feedthru pin; and coupling a connector assembly to the exposed portion of the feedthru pin after the electronic assembly has been encapsulated with the non-metallic hermetic composite.

2. The method of claim 1, wherein encapsulating the electronic assembly with the non-metallic hermetic composite comprises applying an inorganic coating to the electronic assembly.

3. The method of claim 2, wherein encapsulating the electronic assembly with the non-metallic hermetic composite comprises applying a layer of parylene to the electronic assembly.

4. The method of claim 2, wherein the inorganic material is selected from the group consisting of silicon nitride, silicon dioxide, and silicon oxinitride.

5. The method of claim 2, wherein applying the inorganic coating to the electronic assembly comprises reactive sputtering.

6. The method of claim 1, further comprising:
mounting a rechargeable power source to the electronic assembly; and
encapsulating the rechargeable power source with the non-metallic hermetic composite.

7. The method of claim 6, wherein the rechargeable power source is mounted to the printed circuit board opposite the one or more electronic components.

8. An implantable medical device, comprising:
an electronic assembly comprising a circuit board and one or more electronic components mounted to the circuit board;
a feedthru pin electrically coupled to the electronic assembly;
a non-metallic hermetic composite encapsulating the electronic assembly, wherein at least a portion of the feedthru pin is not encapsulated by the non-metallic hermetic composite;
a connector assembly coupled to the at least a portion of the feedthru pin; and
a layer of impact resistant epoxy disposed over the electronic assembly and connector assembly.

9. The implantable medical device of claim 8, wherein the non-metallic hermetic composite comprises an inorganic coating.

10. The implantable medical device of claim 9, wherein the non-metallic hermetic composite comprises a layer of parylene.

11. The implantable medical device of claim 9, wherein the inorganic material is selected from the group consisting of silicon nitride, silicon dioxide, and silicon oxinitride.

12. The implantable medical device of claim 8, further comprising a rechargeable power source to the electronic assembly, wherein the rechargeable power source is encapsulated with the non-metallic hermetic composite.

13. The implantable medical device of claim 12, wherein the rechargeable power source is mounted to the printed circuit board opposite the one or more electronic components.

14. The implantable medical device of claim 8, wherein the epoxy layer is in contact with the non-metallic hermetic composite.

15. The implantable medical device of claim 8, further comprising a soft material encapsulating the electronic assembly and connector assembly.

16. The implantable medical device of claim 15, wherein the soft material is in contact with the epoxy layer.

17. The implantable medical device of claim 15, wherein the soft material comprises silicone rubber.

18. The implantable medical device of claim 15, further comprising suture holes formed in the soft material.

19. A method of forming an implantable medical device, comprising:
providing an electronic assembly comprising a circuit board and one or more electronic components mounted on the circuit board;
electrically coupling a feedthru pin to the electronic assembly;
encapsulating the electronic assembly with a non-metallic hermetic composite to seal the electronic assembly from a body environment, wherein at least a portion of the feedthru pin is exposed;
coupling a connector assembly to the exposed portion of the feedthru pin after the electronic assembly has been encapsulated with the non-metallic hermetic composite; and
applying a layer of impact resistant epoxy to the electronic assembly and connector assembly after encapsulating the electronic assembly with the non-metallic hermetic composite.

20. The method of claim 19, wherein the epoxy layer is applied directly onto the non-metallic hermetic composite.

21. The method of claim 19, further comprising encapsulating the electronic assembly and connector assembly with a soft material after applying the layer of impact resistant epoxy to the electronic assembly.

22. The method of claim 21, wherein the soft material is applied directly over the epoxy layer.

23. The method of claim 21, wherein the soft material comprises silicone rubber.

24. The method of claim 21, further comprising forming suture holes in the soft material.

25. The method of claim 19, wherein encapsulating the electronic assembly with the non-metallic hermetic composite comprises applying an inorganic coating to the electronic assembly.

26. The method of claim 25, wherein encapsulating the electronic assembly with the non-metallic hermetic composite comprises applying a layer of parylene to the electronic assembly.

* * * * *